(12) United States Patent
Asirvatham

(10) Patent No.: US 12,161,868 B2
(45) Date of Patent: Dec. 10, 2024

(54) WEARABLE DEVICE WITH TRAGUS MODULATION SYSTEM

(71) Applicant: Mayo Foundation for Medical Education and Research, Rochester, MN (US)

(72) Inventor: Samuel J. Asirvatham, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 328 days.

(21) Appl. No.: 17/577,724

(22) Filed: Jan. 18, 2022

(65) Prior Publication Data

US 2022/0212010 A1 Jul. 7, 2022

Related U.S. Application Data

(63) Continuation of application No. 16/879,386, filed on May 20, 2020, now Pat. No. 11,260,228.

(60) Provisional application No. 62/850,976, filed on May 21, 2019.

(51) Int. Cl.
*A61N 1/36* (2006.01)
*A61N 1/04* (2006.01)
*G16H 40/67* (2018.01)

(52) U.S. Cl.
CPC ....... *A61N 1/36039* (2017.08); *A61N 1/0456* (2013.01); *A61N 1/36114* (2013.01); *A61N 1/36139* (2013.01); *A61N 1/36175* (2013.01); *G16H 40/67* (2018.01)

(58) Field of Classification Search
CPC ........... A61B 5/0531; A61B 5/24; A61B 5/40; A61B 5/4836; A61B 5/6803; A61B 5/6898; A61F 2007/0005; A61N 1/0412; A61N 1/0456; A61N 1/0502; A61N 1/36014; A61N 1/36025; A61N 1/36036; A61N 1/36039; A61N 1/36114; A61N 1/36139; A61N 1/36175; A61N 1/3956; A61N 7/00; G16H 20/40; G16H 40/63; G16H 40/67
See application file for complete search history.

(56) References Cited

U.S. PATENT DOCUMENTS

| | | |
|---|---|---|
| 7,797,042 B2 | 9/2010 | Dietrich et al. |
| 7,885,709 B2 | 2/2011 | Ben-David |
| 9,415,220 B1 | 8/2016 | Spinelli et al. |
| 11,260,228 B2 | 3/2022 | Asirvatham |
| 2006/0122675 A1 | 6/2006 | Libbus et al. |
| 2008/0051852 A1 | 2/2008 | Dietrich et al. |
| 2012/0029591 A1 | 2/2012 | Simon et al. |
| 2017/0027812 A1 | 2/2017 | Hyde et al. |

(Continued)

FOREIGN PATENT DOCUMENTS

| | | |
|---|---|---|
| WO | WO 2018/039458 | 3/2018 |
| WO | WO 2018/050773 | 3/2018 |

*Primary Examiner* — George Manuel
(74) *Attorney, Agent, or Firm* — Fish & Richardson P.C.

(57) ABSTRACT

A wearable device combines its existing functions (e.g., a headphone) with non-invasive autonomic modulation using tragus or other external auditory meatus stimulation. The wearable device can output audio to a user, such as music, podcast, etc., and further provide modulation of the vagus nerve via tragus stimulation or other external auditory meatus stimulation to treat various diseases.

13 Claims, 6 Drawing Sheets

(56) References Cited

U.S. PATENT DOCUMENTS

| | | |
|---|---|---|
| 2017/0078785 A1 | 3/2017 | Qian et al. |
| 2017/0087364 A1 | 3/2017 | Cartledge et al. |
| 2018/0133507 A1 | 5/2018 | Malchano et al. |
| 2019/0001129 A1* | 1/2019 | Rosenbluth .............. A61N 1/08 |
| 2020/0368527 A1 | 11/2020 | Asirvatham |

* cited by examiner

WEARABLE DEVICE WITH TRAGUS MODULATION SYSTEM

CROSS-REFERENCE TO RELATED APPLICATIONS

This application is a continuation of U.S. application Ser. No. 16/879,386 filed on May 20, 2020, which claims the benefit of U.S. Application Ser. No. 62/850,976, filed May 21, 2019. The disclosure of the prior applications are considered part of (and are incorporated by reference in) the disclosure of this application.

TECHNICAL FIELD

This document describes devices, systems, and methods related to tragus or other external auditory meatus modulation.

BACKGROUND

Peripheral methods to modulate the autonomic nervous system have been done via acupuncture or acupressure. Some device-based stimulation has been used in cardiac rhythm disorder treatment, as well as treating some forms of epilepsy, depression, appetite control, and a few other disorders. A particular branch of the vagus nerve is intracranial, and innervates the tragus and part of the external auditory meatus. Low level stimulation of the tragus has been used. However, such typical devices and methods of stimulation are cumbersome and not part of everyday use technology.

SUMMARY

Some embodiments described herein include a wearable device that combines its existing functions (e.g., a headphone) with non-invasive autonomic modulation using tragus or other external auditory meatus stimulation. For example, the wearable device is configured to output audio to a user, such as music, podcast, etc., and further provide modulation of the vagus nerve via tragus stimulation or other external auditory meatus stimulation to treat various diseases, such as cardiovascular, neurologic, and/or gastroenterological illnesses. The wearable device can be worn or engaged with a non-invasive body portion, such as an external ear, an auditory canal, and other suitable body areas.

The wearable device can include an electroporation circuit to provide tragus stimulation. In addition, the wearable device can be configured to provide an inhibitory signal to the tragus area to detect signals and parameters for autonomic tone and transmit a reversible electroporation sequence based on the detected signals and parameters if the stimulatory signal is found to result in, or likely to cause, an undesired effect.

The wearable device can include a filtering circuit configured to prevent the stimulatory and/or inhibitory signals from interfering with the audio signal (e.g., music) outputted from the wearable device. For example, the filtering circuit can generate a signal that can cancel a noise from the stimulatory and/or inhibitory signals, thereby providing clarity in audio output from the wearable device.

The wearable device can include a validation circuit configured to validate that the stimulatory and/or inhibitory signals have targeted and resulted in desired physiological effects. For example, the validation circuit can generate a reversible electroporation signal to validate whether perceived signals are indeed the transmitted signals or merely represent noise.

The wearable device can include a feedback circuit that detects autonomic tone based on various sensor inputs, and controls generation and/or transmission of the stimulatory and/or inhibitory signals.

Particular embodiments described herein include a wearable device including a housing configured to be removably attached adjacent to a tragus area; a speaker configured to generate sound based on the sound signal; a sensor configured to detect physiological or neurological parameters; electrodes configured to deliver electric signals; a processing device; and a memory device storing instructions that when executed by the processing device cause the wearable device to perform operations comprising: outputting audio using the speaker; generating a stimulatory signal; applying the stimulatory signal on the tragus area to increase vagal tone; detecting a signal for autonomic tone; determining that a vagal input exceeds a threshold value; generating an inhibitory signal that represents a reversible electroporation sequence; and applying the inhibitory signal on the tragus area.

In some implementations, the system can optionally include one or more of the following features. The stimulatory signal can be DC signal. The inhibitory signal can be inverse to the stimulatory signal. At least one of the stimulatory signal and the inhibitory signal can use nanosecond pulse widths and/or relatively high amplitude. At least one of the stimulatory signal and the inhibitory signal can use electroporation targeting sensory nerves and sensory impulses from vagus afferents. A frequency of the stimulatory signal and/or an electroporative pulse of the inhibitory signal can be determined based on a site to which the stimulatory signal and/or the inhibitory signal are applied. The operation can further include generating an inverse signal for the stimulatory signal and/or the inhibitory signal; injecting the inverse signal into the audio signal to cancel the stimulatory signal and/or the inhibitory signal to not interfere with user's auditory experience of the audio signal. The operation can further include creating a template for the stimulatory signal and the inhibitory signal, wherein the inverse signal is generated based on the template. The operation can further include generating a reversible electroporation sequence; and validating autonomic neural recordings based on the reversible electroporation sequence. The reversible electroporation sequence can be a small phased DC sequence. The operation can further include generating pulsed DC sequences as a negative effector; and applying the pulsed DC sequences to temporarily and reversibly electroporate vagal afferents. The operation can further include detecting, using a sensor, a predetermined parameter representative of autonomic tone; and determining when to simulate, how much to stimulate, and when to block based on the predetermined parameter. The predetermined parameter can include a local electroneural and thermal conductivity. The operation can further include detecting, using a neural network based learning algorithm, an individual's physiological parameter; determining that there is an adverse detection of autonomic tone; and enabling preemptive change in the stimulatory signal and/or the inhibitory signal. The physiological parameter can include a heart rate variability.

Particular embodiments described herein include a method for stimulating a tragus. The method can include generating and outputting, using a wearable device, an audio signal; generating, using the wearable device, a stimulatory signal; applying, using the wearable device, the stimulatory signal on a tragus area to increase vagal tone, wherein the wearable device is arranged at the tragus area; detecting a signal for autonomic tone; determining that a vagal input exceeds a threshold value; generating, using the wearable device, an inhibitory signal that represents a reversible electroporation sequence; and applying, using the wearable device, the inhibitory signal on the tragus area.

In some implementations, the system can optionally include one or more of the following features. At least one of the stimulatory signal and the inhibitory signal can use nanosecond pulse widths and/or relatively high amplitude. At least one of the stimulatory signal and the inhibitory signal can use electroporation targeting sensory nerves and sensory impulses from vagus afferents. A frequency of the stimulatory signal and/or an electroporative pulse of the inhibitory signal can be determined based on a site to which the stimulatory signal and/or the inhibitory signal are applied. The method can further include generating an inverse signal for the stimulatory signal and/or the inhibitory signal; injecting the inverse signal into the audio signal to cancel the stimulatory signal and/or the inhibitory signal to not interfere with user's auditory experience of the audio signal. The method can further include creating a template for the stimulatory signal and the inhibitory signal, wherein the inverse signal is generated based on the template. The method can further include generating a reversible electroporation sequence; and validating autonomic neural recordings based on the reversible electroporation sequence. The reversible electroporation sequence can be a small phased DC sequence. The method can further include generating pulsed DC sequences as a negative effector; and applying the pulsed DC sequences to temporarily and reversibly electroporate vagal afferents. The method can further include detecting, using a sensor, a predetermined parameter representative of autonomic tone; and determining when to simulate, how much to stimulate, and when to block based on the predetermined parameter. The predetermined parameter can include a local electroneural and thermal conductivity. The method can further include detecting, using a neural network based learning algorithm, an individual's physiological parameter; determining that there is an adverse detection of autonomic tone; and enabling preemptive change in the stimulatory signal and/or the inhibitory signal. The physiological parameter can include a heart rate variability.

The devices, system, and techniques described herein may provide one or more of the following advantages. Some embodiments described herein include a wearable device with tragus or other external auditory meatus stimulation, which is for easy and daily use. Further, the wearable device provide a non-invasive way to perform tragus or external auditory meatus stimulation. Moreover, the tragus or external auditory meatus stimulation is combined with music and auditory stimulation that provides mood altering and autonomic neural modulatory effects.

The details of one or more implementations are set forth in the accompanying drawings and the description below. Other features and advantages will be apparent from the description and drawings, and from the claims.

DETAILED DESCRIPTION OF ILLUSTRATIVE EMBODIMENTS

Figure 1:
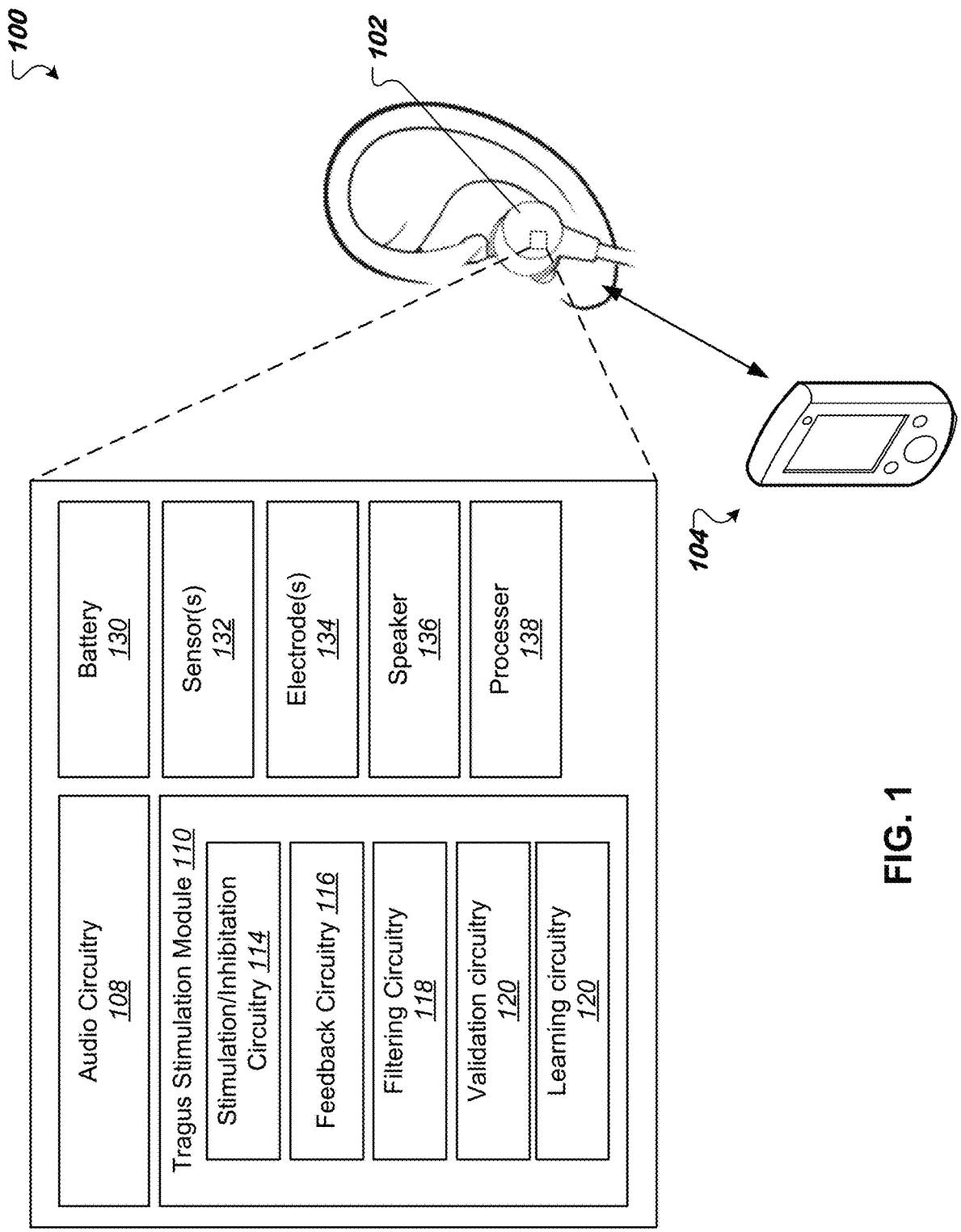
FIG. 1 is a block diagram of an example system for tragus stimulation.

FIG. 1 is a block diagram of an example system 100 for tragus stimulation. The system includes a wearable device 102 which can have various medical or non-medical functions. For example, the wearable device 102 can include electromechanical devices that produce sound, such as headphones, earplugs, earphones, earbuds or headsets. The wearable device can be of other suitable types of wearable forms with various functionalities. The wearable device 102 has a housing configured to be worn or engaged with a suitable body portion, such as a tragus area or other external auditory meatus areas. In the illustrated example, the wearable device 102 is an earbud engageable with a tragus area.

The wearable device 102 can communicate with a computing device 104 via various communications interface, such as Bluetooth, NFC, Wi-Fi, other wireless interfaces, and/or wired interfaces. In some implementations, the computing device 104 can be used to perform at least part of the processes of the wearable device 102 described herein. In addition or alternatively, the computing device 104 can be used to interact with a user wearing the wearable device 102 and enable the user to provide inputs or feedbacks to the wearable device 102 or other remote computing devices, such as a server. In addition or alternatively, the computing device 104 can be used provide audio (e.g., music, podcast, etc.) to the wearable device 102 so that the user can consume such audio via the wearable device 102.

The wearable device 102 can include audio circuitry 108 configured to generate sound via, for example, a speaker 136 in the wearable device 102. The wearable device 102 can receive a sound signal from a remote device, such as the computing device 104, and generate the sound based on the sound signal.

The wearable device 102 can further include a tragus stimulation module 110 having stimulation/inhibition circuitry 114, feedback circuitry 116, filtering circuitry 118, validation circuitry 120, and learning circuitry 122.

The stimulation/inhibition circuitry 114 is configured to generate a stimulatory signal and an inhibitory signal, which can be transmitted via, for example, electrodes 134 of the wearable device 102. The electrodes 134 can be arranged at or adjacent a target body portion of a user, such as a tragus or other external auditory meatus, when the wearable device 102 is worn by the user. Other signals can also be generated and transmitted by the stimulation/inhibition circuitry 114.

The feedback circuitry 116 can receive signals from sensors 132 that are configured to detect various physiological, neurological, and/or other suitable signals and parameters. For example, the feedback circuitry 116 can detect autonomic tone based on various sensor inputs from the sensors 132, and control (e.g., adjust) generation and/or transmission of the stimulatory and/or inhibitory signals (e.g., when to stimulate, how much to stimulate, when to block, etc.).

The filtering circuitry 118 can generate and transmit a signal that prevents the stimulatory and/or inhibitory signals from interfering with the audio signal (e.g., music) from the audio circuitry 108. For example, the signal from the filtering circuitry 118 can be configured to cancel a noise from the stimulatory and/or inhibitory signals, thereby providing clarity in audio output from the wearable device.

The validation circuitry 120 operates to validate the stimulatory and/or inhibitory signals from the stimulation/inhibition circuitry 114. For example, the validation circuitry 120 can validate that the stimulatory and/or inhibitory signals have resulted in desired effects. For example, the validation circuitry 120 can generate a reversible electroporation signal to validate whether perceived signals are indeed the transmitted signals or merely represent noise The learning circuitry 122 can be configured to monitor, learn, and predict a user's physiological, neurological, and/or other parameters (e.g., heartrate variability and other sensory parameters). Such prediction can be used to provide preemptive change in the stimulatory and/or inhibitory signals. For example, the learning circuitry 122 include a real-time neural network learning machine that, if there is an adverse detection of autonomic tone with implication being either susceptibility to syncope or arrhythmia, predicts and preemptively changes the stimulatory or inhibitory sequence, even before the actual parameter concerned drops or changes such as the onset of an arrhythmia.

The wearable device 102 can include a processing device 138 configured to at least partially execute the processes in the wearable device including the audio circuitry 108 and the tragus stimulation module 110. The wearable device 102 can include a battery 130 to supply power to the components in the wearable device.

The wearable device 102 can be implemented using at least some of the components described in FIG. 5 and/or FIG. 6 below.

Figure 2:
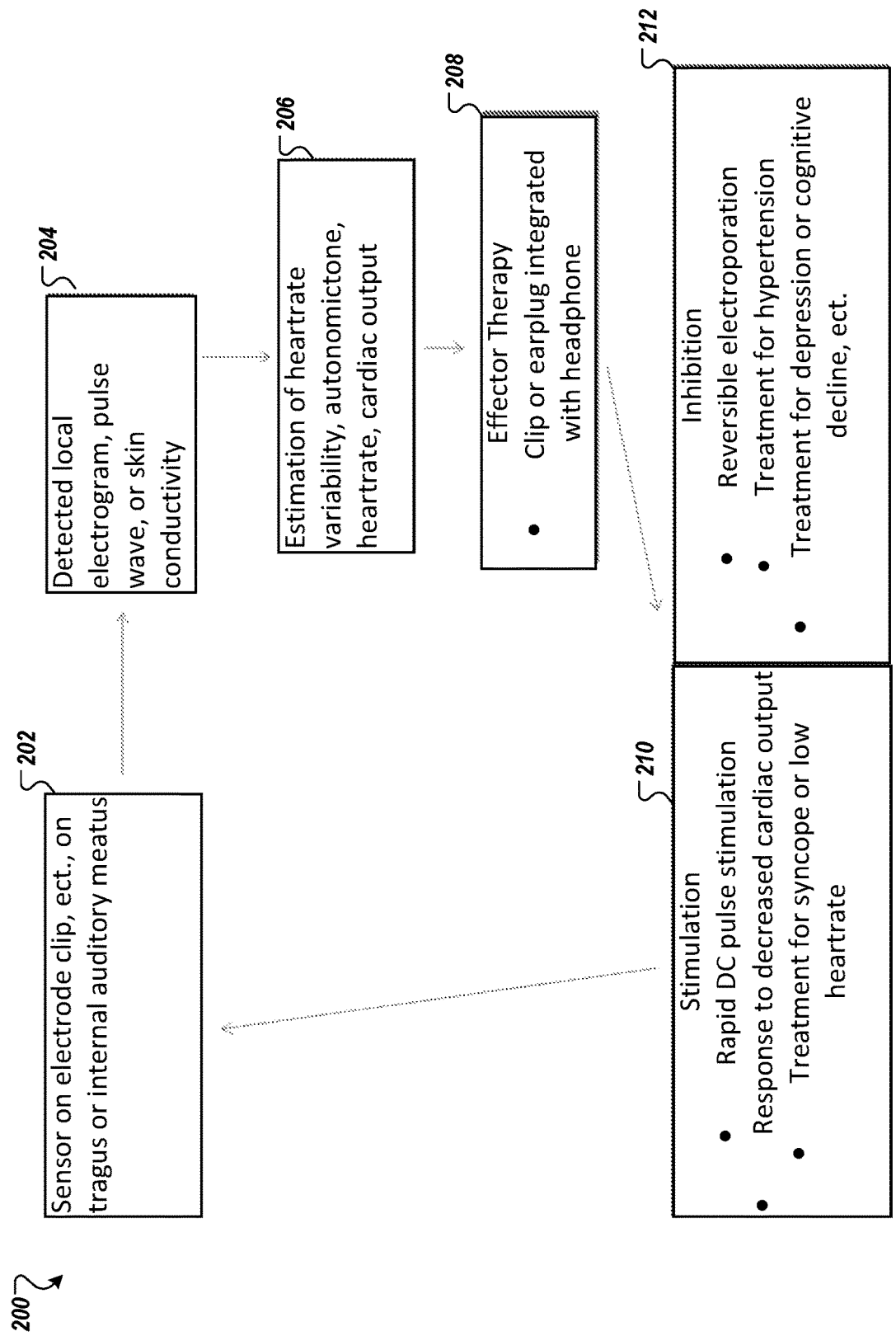
FIG. 2 illustrates an example closed loop process of tragus or other external auditory meatus stimulation using a wearable device.
Figure 3:
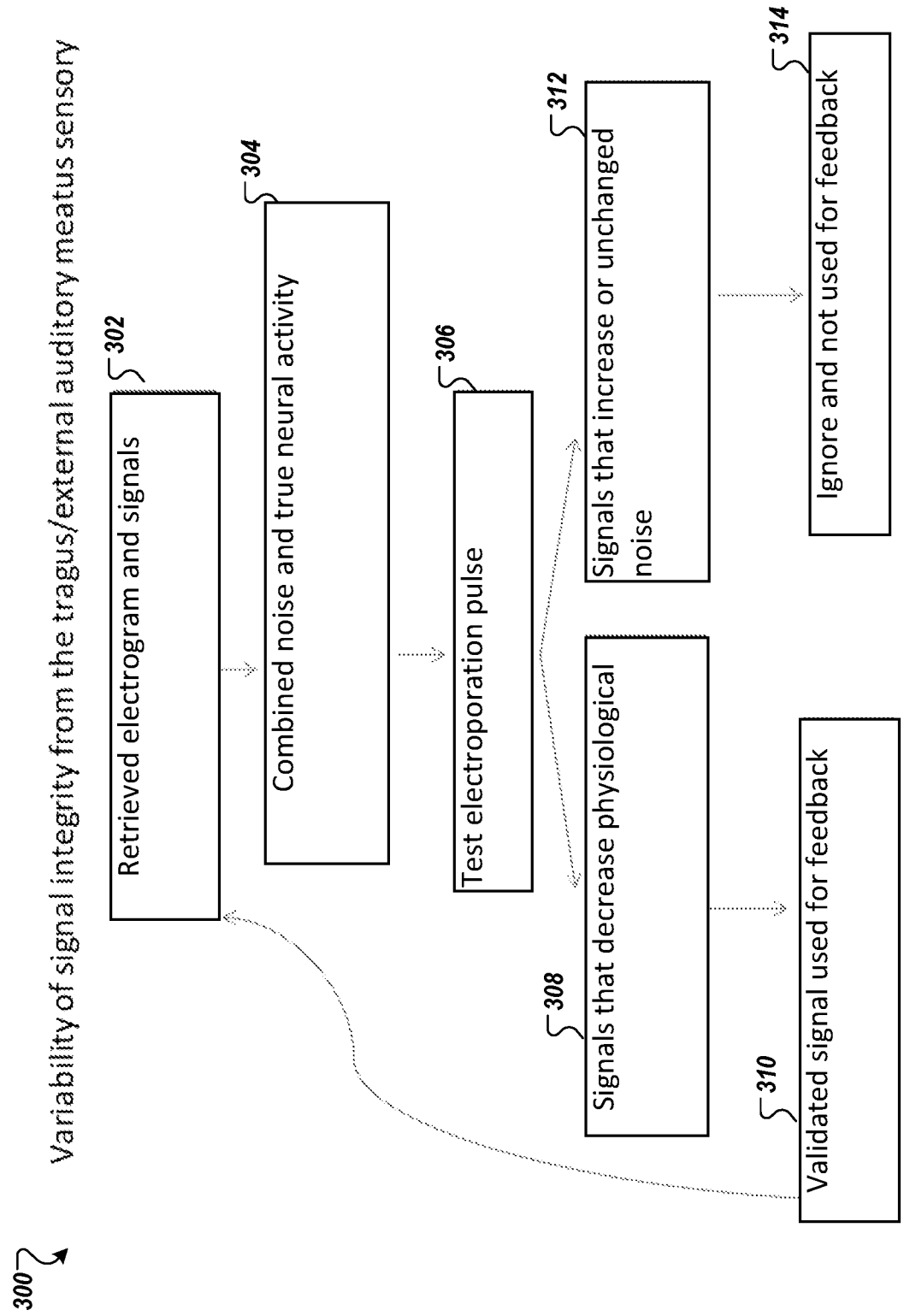
FIG. 3 illustrates an example process of testing integrity of a signal detected from the tragus or other external auditory meatus and filtering a noise from the detected signal.
Figure 4:
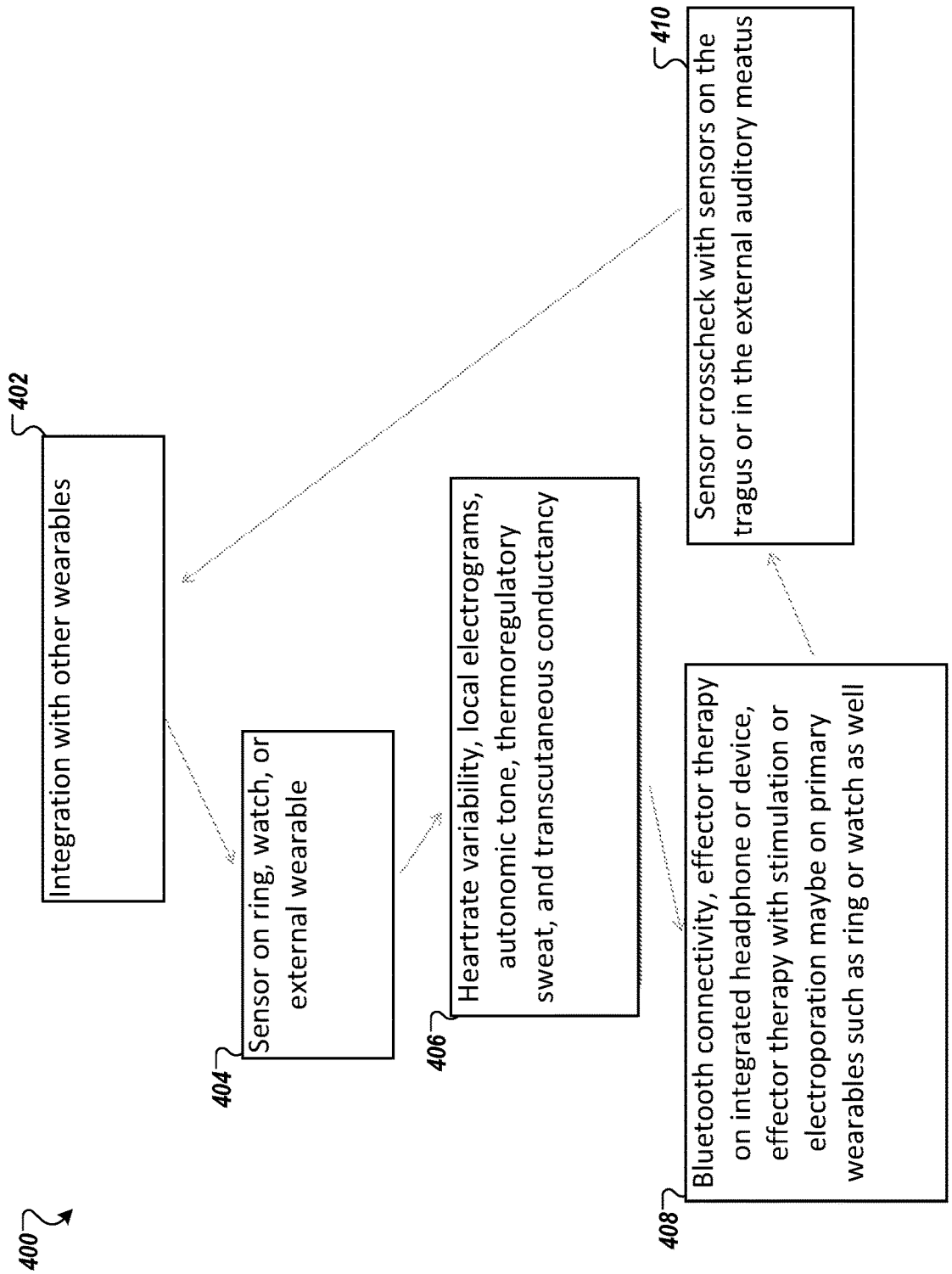
FIG. 4 illustrates an example operation of using a sensor in the wearable device.

Referring to FIGS. 2-4, example operations of the wearable device 102 are described. In particular, FIG. 2 illustrates an example closed loop process 200 of the tragus or other external auditory meatus stimulation using the wearable device 102. FIG. 3 illustrates an example process 300 of testing integrity of a signal detected from the tragus or other external auditory meatus, and filtering a noise from the detected signal. FIG. 4 illustrates an example operation 400 of using a sensor in the wearable device 102.

Referring to FIG. 2, the wearable device 102, which can be clipped on the tragus or auditory meatus (external or internal), includes a sensor that detects physiological, neurological, and/or other parameters from the area (Block 202). For example, the sensor operates to detect local electrogram, pulse wave, or skin conductivity (Block 204), and the wearable device 102 (and/or a computing device connected to the wearable device 102) can analyzed the detected parameters and estimate heartrate variability, autonomic tone, heartrate, cardiac output, and/or other parameters (Block 206). With such estimation, effector therapy can be performed using the wearable device 102 (e.g., clip or earplug integrated with a headphone) (Block 208). As described herein, the wearable device 102 can provide a simulation signal, which can be a rapid DC pulse stimulation (Block 210). The stimulation signal can be generated in response to decreased cardia output. The stimulation can be performed to treat syncope, low heartrate, and/or other diseases. The wearable device 102 can provide an inhibition signal, which can be a reversible electroporation (Block 212). The inhibition signal can be used to treat hypertension. The inhibition signal can also be used to treat depression, cognitive decline, and/or other diseases. While the stimulation and/or inhibition are performed, the wearable device 102 can continue to use the sensor to detect the parameters (return to Block 202 and subsequent Blocks). The operations of the wearable device 102 in FIG. 2 are further described herein.

Referring to FIG. 3, the wearable device 102 and/or a computing device connected to the wearable device 102 can test integrity of signals from the tragus or external auditory meatus sensory. For example, the wearable device 102 and/or a connected computing device can retrieve electrogram and signals sensed from the tragus or external auditory meatus (Block 302), and analyze combined noise and true neural activity (Block 304). The wearable device 102 and/or a connected computing device can test a electroporation pulse (Block 306). If signals are found to decrease physiological parameters (Block 308), the signals are validated and used for feedback (Block 310). If signals are found to increase or unchange noise (Block 312), the signals are ignored and not used for feedback (Block 314). The operations of the wearable device 102 in FIG. 3 are further described herein.

Referring to FIG. 4, the system described herein can be integrated with a variety of wearable devices (Block 402). One or more sensors can be disposed in such wearable devices, such as ring, watch, and other external wearables (Block 404). The system integrated with the wearables can be used to detect heartrate variability, local electrograms, autonomic tones, thermoregulatory sweat, transcutaneous conductancy, and other parameters (Block 406). Such wearables can provide Bluetooth or other wireless connectivity and is configured to provide effector therapy on integrated headphone or other devices (Block 408). Such effector therapy with stimulation and/or electroporation can be provided on primary wearables such as ring or watch as well. The system can further provide sensor crosscheck with the sensors on the tragus or in the external auditory meatus (Block 410). The operations described in FIG. 4 are further described herein.

As described herein, some embodiments described herein include a wearable device that combines an existing function (e.g., headphone) with direct autonomic modulation via tragal stimulation. The wearable device can be of various types with medical or non-medical functions, such as headphones, earplugs, earphones, earbuds or headsets. The wearable device further includes circuitry for direct tragus stimulation and automated feedback from the stimulation. The feedback can be obtained based on local electrograms, skin impedance characteristics, and/or measured heartrate.

For example, the wearable device can be configured as a headphone or the like, and include a clipped-on stimulatory electrode component for the tragus. The wearable device is configured to provide autonomic modulation that involves standard auditory or music entering through the wearable device (e.g., earphone), along with phasic varied level stimulation of the tragus.

The wearable device can be formed in various configurations and designs. For example, the wearable device is a headphone which covers the ear completely and encloses through a portion of the headphone the clip or skin electrode that is in contact with the tragus. In another example, the wearable device is an earbud that is capable of vibration for direct vibratory stimulation of the tragus and the external auditory meatus itself.

In some implementations, the tragus stimulatory electrode component of the device can be used for a standalone self-administered therapy based on the type of disorder and the type of treatment required.

In other implementations, because the tragus stimulatory electrode component is integrated with commonly used devices (e.g., earphone or headphone), the wearable device can be administered while music or other auditory phenomena are being experienced.

In yet other implementations, the wearable device can be a specific pairing of an auditory stimulation with tragus stimulation. For example, the type of music and the type of stimulation are specifically engineered for a desired complimentary effect.

In yet other implementations, the tragus stimulatory clip of the device can record superficial skin conductance. In addition or alternatively, the device can include a specific filtering system and further record peripheral autonomic neural activity via the electroneurograms. As a result, a feedback loop can be set up where the autonomic tone is monitored. Further, as a result of the level of existing autonomic tone, the type of stimulation and/or musical experience can be modulated.

In addition or alternatively, the wearable device can include several additional features. For example, the wearable device can include a pulse wave Doppler probe to analyze the pulse waveform, automatically calculate heart rate variability, and/or couple this information with neural signals and skin conductance.

As described herein, some embodiments described herein provides devices and methods for non-invasive modulation of the vagus nerve via a non-invasive and portable DC electroporation unit. This can be applied to various diseases as described herein. Further, the utility of DC electroporation via portable use to a non-invasive site, such as the external ear, the auditory canal, the vagus, etc., can be leverage for treatment of other diseases.

Multiple diseases involving the cardiovascular, neurologic, and gastroenterological systems can be treated with the use of DC electroporation via modulation of the nervous system, such as the vagus nerve. These often involve invasive procedures that are dangers. Further, despite invasive and direct visualization for modulation, such invasive procedures still may fail.

The devices and methods described herein provide means to non-invasively stimulate modulation of the vagus nerve via DC electroporation. In some implementations, a wearable device can be configured to incorporate a DC electroporation unit. A wearable device (e.g., earbuds) is configured as a portable and removable device and further configured to deliver treatment in the form of DC electroporative doses. Such a device can include a connector for plugging in to an energy source such as a cell phone or pocket battery, and/or an interface that receives energy remotely from an energy source (e.g., via RF transmission). For example, the wearable device is configured in the form of earbuds that can conform to the outer ear canal. The earbuds can include a plurality of electrodes and spacing for optimal DC delivery. In another example, the wearable device is configured in the form of an ear piercing with DC electrodes. The ear piercing can be placed in regions of interest of the ear, especially the tragus of the ear. Such an ear piercing form of the wearable device can be used for short and/or long term recording/stimulation. In yet another example, the wearable device can be configured as a subcutaneous device which can be placed under the skin. Such wearable devices can be configured as miniaturized devices. Such wearable devices can include a rechargeable battery as a power source. For example, wearable devices can be used with transference devices that can be located at desired places (e.g., in a bedroom) where the wearable devices can be recharged conveniently (e.g., overnight while sleeping).

The wearable device can be coupled to various types of energy sources, such as DC electroporation, ultrasound/sonication, radio frequency, cryoenergy, microwave energy, chemical delivery, and/or other suitable energy sources. Such energy sources can be used simultaneously, in combination, in series, or as discrete, timed delivery.

The wearable device can include a power source (e.g., a rechargeable battery) to power the wearable device for DC delivery. Such a power source can be of various types, such as from a port in a cell phone, a pocket battery, a rechargeable source, a recharging via RF transmission, a rechargeable unit located in a patient's bedroom for overnight charging, and other suitable power sources.

The delivery of DC energy can be altered in a plurality of ways. For example, a DC energy can be delivered by changing frequency and/or duration of the DC pulse, and/or the number of the pulses. In addition, this can be connected via a feedback circuit with ongoing monitoring and/or time set delivery which can be adapted by a cell-phone controlled and algorithm based delivery mechanism. In addition, this can be a preset/pre-specified "prescription" per individual depending on the disease and desired treatment effect.

The wearable device and/or the computing device (e.g., a mobile device) communicatively connected to the wearable device can actively monitor the DC delivery output. For example, multiple monitoring of physiologic parameters can be performed via, e.g., the ear buds and portable unit. Such physiological parameters being monitored can include heart rate, heart rate variability, and other desired parameters. In some implementations, such parameters can be obtained from pulsations of the carotid or blood flow monitoring through the external ear vasculature. In addition, the wearable device (e.g., ear buds) can include functionality of temperature sensing, accelerometer based for activity monitoring and positioning, and skin impedance. The monitored parameters allow for surrogacy of vagal nerve stimulation.

The wearable device can be configured to be positioned or worn in various body locations, such as piercings of the navel, tragus, eyebrow, tongue, lip, and other suitable body locations. In addition or alternatively, the wearable device can be configured in the form of a ring having an electrode so that the electrode in the ring is arranged on a finger/thumb or toe. Alternatively or in addition, the wearable device can be configured in the form of a cap (e.g., baseball cap, winter hat, sweater hood, etc.) having electrodes that are arranged on sides above the ear when the cap is worn. Alternatively or in addition, the wearable can be configured in the form of a belt buckle, a shirt pocket lining, sneakers, or other suitable items.

The wearable device can include a biofeedback system for monitoring cardiac, autonomic, neurologic response, and other suitable biological responses. In addition to vagal stimulation (or inhibition) circuitry, the wearable device can include a biofeedback circuitry. For example, the wearable device (e.g., earbuds) can record a far-field EEG that can be processed for neurologic purposes. The wearable device can further serve as a return electrode to widen the antenna for cardiac recording. In some implementations, the earbuds can be connected via a headset with interloping band (e.g., traditional headsets/speakerphones) in order to serve as a unit that can include multiple electrodes for EEG recording and/or ECG for recording heart rate. The utility of these signals could be integrated into a feedback mechanism for input/output control, recording, transmissions, and primed for signal processing for increased signal recognition and deciphering. The method/algorithms can also include heart rate variability and heart rate spectral analysis.

The wearable device can be configured to provide titration with energy and/or music. For example, the wearable can deliver various tones and frequencies of music to provide an additive effect which may permit lower doses of DC energy to be delivered. This delivery can be performed in combination, in sequence, additive/summative, and in pre-specified algorithms, timing during day/night cycles.

The wearable device, such as earbuds, having DC electroporation capability described herein can be used to treat various diseases, such as cardia diseases (e.g., cardiac arrhythmias, heart failure, etc.), neurologic diseases (e.g., chronic dizziness/vertigo, cognition enhancement, depression, epilepsy, autism, motion sickness, etc.), gastroentestinal diseases (e.g., chronic constipation, gastroparesis from diabetes, bowel mobility, weight loss, etc.), and ear/nose/throat (ENT) diseases.

For example, the wearable device is configured and used to treat cardiac arrhythmias by stimulating the vagus nerve, via the tragus, in order to induce or inhibit vagal activity. The wearable device can be used to provide a stimulus that can prevent, decrease the likelihood of arrhythmias, modify the arrhythmias to a more modifiable state, or provide an abrupt elimination/termination or vagolytic defibrillation. The wearable device can be used for those at risk, with known arrhythmias, such as atrial fibrillation where studies have suggested tragus/vagal manipulation may alter cardiac electrophysiology to reduce/eliminate atrial fibrillation. Further, the wearable device can be used to cardiovert with a strong vagus input out of atrial fibrillation, as opposed to external cardiac defibrillation. Moreover, the wearable device can be used with defibrillators in place in order to increase the efficacy of defibrillation, success of defibrillation, and potentially defibrillation with a lower delivery of joules from the ICD component.

The wearable device can be configured and used to treat heart failure by invoking modulation of the vagus nerve in the pathogenesis and ongoing continuum of heart failure. Chronic, intermittent, or sequential pulsations at various times of the day may change the overall sympathetic/parasympathetic system in order to favor more favorable heart failure stability and potentially positive remodeling.

The wearable device can be configured and used to treat chronic dizziness/vertigo. For example, the utility of having earbuds in the external auditory ear canal provides a vantage point to the semilunar canals. The use of DC electroporation and/or ultrasound sonication can be used in combination. The stimulation can be user induced when dizziness occurs. Stimulation can cause activation of mechanotransduction receptors and hair cells, and thus facilitate the movement of endolymphatic flow and movement of otoliths/canaliths. Alternatively, sonication can be used to provide lithotripsy of the otoliths/canaliths to destroy rather than dislodge these particles which create dizziness.

The wearable device can be configured and used for cognition enhancement. For example, the stimulation of the vagus has the potential to improve cognition and thus low-level DC stimulation of the tragus may promote this.

The wearable device can be configured and used to treat depression. For example, stimulation of the vagus can be used to improve depressive symptoms. The wearable device for cognition enhancement and depression treatment can also be used in combination with musical therapy to provide additional benefits in cognition and psyche.

The wearable device can be configured and used to treat epilepsy, such as refractory epilepsy, of which the vantage point of the tragus can provide an ideal position.

The wearable device can be configured and used for potential therapy in autism. For example, stimulation of vagus can provide signals to higher brain centers which can, along with incorporation with music therapy, improve cognition and function in autism.

The wearable device can be configured and used for motion sickness treatments. For example, cruise ship, fishing trip, long travel. Further, the wearable device can also be used for military and/or NASA space astronauts.

The wearable device can be configured and used for gastroentestinal treatment. For example, vagus stimulation provides a strong input to the GI tract motility. This can be of use in patients with chronic constipation or with gastroparesis from diabetes. This can promote bowel motility. The portability and ease of turning on therapy can make this a daily treatable condition. Further, the wearable device can be used for a weight loss strategy by using vagal stimulation/inhibition, cycling, feedback, and circadian stimulation.

The wearable device can be configured and used for ENT treatment, such as chronic otitis externa. For example, the use of ear buds in the external auditory canal can deliver continuous, intermittent, or therapy regulated delivery of DC electroporation to kill bacteria in the canal that are causative of this painful disease. This can provide an option of intermittent sterilization rather than chronic antibiotics.

As described herein, in addition to, or alternatively to, the wearable device that combines a typical functionality (e.g., headphone) with direct tragus stimulation and automated feedback based on, for example, local electrograms, skin impedance characteristics, and measured heartrate, some embodiments described herein provide a wearable device which can fit into the external auditory meatus and include a circumferential pulse sensor for measuring and/or estimating various physiological parameters, such as heartrate, blood pressure, oxygen saturation, cardiac stroke volume, and cardiac output. The wearable device can be of various types with medical or non-medical functions, such as headphones, earplugs, or headsets. The wearable device further includes circuitry having the sensor, or communicatively connected to the sensor, and configured to process signals from the sensor to obtain physiological parameters. The wearable device can be used as a simple monitoring device for measuring physiological parameters for users who use the wearable device for non-medical purposes (e.g., listening to music). In addition, the wearable device can be used as an afferent limb to produce feedback for tragal and external auditory meatus stimulation.

In some implementations, the wearable device can include electrodes arranged as a fine grid and configured to record neural signals and automated subtraction of far-field cardiac signals. This direct feedback is further enhanced with small stimuli that are not meant for tragal stimulation but to assess transcutaneous impedance to even further refine the feedback loop essential for the operation of the system in the wearable device.

Configured as such, the system can be used to treat hypertension (pressure monitor), improve cardiac survival and decrease arrhythmia (heartrate variability), and to treat depression and cognition with patient-based input and feedback.

In some implementations, the system can further include a noise canceling module configured to generate an inverted signal based on the tragal pulse, and input the inverted signal into the wearable device (e.g., headphone) to prevent audio feedback or noise that may compromise the listening experience.

In some implementations, the stimulation signal can be generated in various ways, such as based on reversible electroporation, electrical fields, DC pulse, optogenetic stimulation, and/or magnetic transcranial stimulation. For example, magnetic transcranial stimulation can not only stimulate the vagus nerve but direct cortical stimulation to achieve the functionalities and benefits described herein. Other sources of stimulation may include vibration or focused ultrasound.

In addition, the system can provide continuous monitoring and establish templates for a particular patient and patient profile so that any input data serve as a learning algorithm to understand future events, predict alarming trends including with deep learning networks and automated alert systems.

Referring still to FIGS. 1-4, the tragus stimulation system described herein is configured to perform reversible and irreversible electroporation from all the iterations including the external auditory meatus and tragus combined approaches. Instead of focusing on stimulation simply due to a perceived need to increase vagal tone as the only source of benefit, the system described herein is configured to selectively change a particular modality in both directions, i.e., stimulation and inhibition. With such an inhibitory arm, the system can operate to detect signals and parameters for autonomic tone, and, based on the detected signals and parameters, send a reversible electroporation sequence if a vagal input is found to be too strong to result in syncope or even cardiac arrest. As such, for example, the system can respond to precipitous drops in heartrate or blood pressure. Further, the inhibitory arm of the system can effectively treat several diseases, such as syncope, excessive sinus bradycardia, bowel dysmotility disorders, and cognitive benefit.

Further, the system can provide painless stimulatory and inhibitory delivery for therapy by using nanosecond pulse widths and relatively high amplitude. Although such small pulse widths and high amplitude may cause interference with the audio signals from the device, a filtering circuitry described herein can prevent such interference with the audio signals. In addition or alternatively, painless stimulatory and inhibitory delivery of the system can be performed by using electroporation specifically targeting sensory nerves and sensory impulses even from the vagus afferents that still allow sending stimulatory signals via the autonomic fibers. For example, the disjoint between free nerve endings and myelinated as well as unmyelinated, including c-fibers, have differences in their thresholds for electroporation, specifically allowing only sending signals through the autonomics.

The system described herein can provide multichannel sensing and stimulatory and inhibitory outputs. For example, there may be different requirements for different applications, e.g., heart-related applications, cognitive applications, and other applications. The system provides multichannel sensing so that specific sites can be stimulated at frequencies different from, and/or inhibited with electroporative pulses different from, other sites based on the regional differences on organ benefit from various sites of sympathetic and vagal afferents.

The system can be incorporated in audio headphones, video VR/AR devices, and other types of wearable devices, and configured to handle conflicting signals in both directions as described herein. Further, the system herein can provide a mechanism that ensures an audio quality of a wearable device (e.g., a headphone) that incorporates the system. For example, signals (e.g., stimulatory and inhibitory sequences) generated by the system incorporated in a wearable device may cause artifacts that ruin the audio experience from the wearable device. The system of the present disclosure includes a filtering circuit that cancels noises from the stimulatory and inhibitory signals, thereby providing clarity in audio output from the wearable device. As described herein, the filtering circuit can create a template for various pulse sequences (e.g., stimulatory and inhibitory sequences), and automatically inject an inverse signal into an audio signal from the wearable device to cancel any interference of the stimulatory signal and/or inhibitory signal with the audio output from the wearable device. The inverse signal can be configured to make the arithmetic sum to be zero when combined with a corresponding stimulatory and/or inhibitory signal.

In some implementations, a wearable device of the system can be configured to be capable of various types of wired and/or wireless connection, such as Bluetooth, NFC, and other suitable wireless connections with other devices, such as watches, monitoring devices, ECG shirts, etc. the wearable device and the other devices connected with the wearable device can be configured to enable a patient wearing it to use and create an appropriate feedback. Further, the tragus can serve as a sensory port alone to allow for feedback effector therapies at other sites including with implanted devices.

The system described herein is configured to validate the signals by generating a partial stimulatory sequence to see if a desired physiological effect occurs, thereby validating a specific spatial location of nerve fibers. In some implementations, the system operates to generate reversible electroporation as an automated or manually administered test to validate whether the perceived signals are indeed genuine or simply represent noise. For example, direct neural recording is very difficult to filter from noise. However, if we send a small reversible electroporation sequence, a noise will not be affected whereas neural signals will decrease critical validation piece for any invention in this area that involves feedback to work.

In addition to a wearable device (e.g., a headphone) with stimulatory electrodes including on the tragus and within the external auditory meatus, the system can include balloon-based electrodes within the external auditory meatus to audio inputs from the headphones themselves being assessed for positive or negative effects on the central nervous system. Further, the system can use artificial intelligence algorithms to validate perceived signals so as to provide the feedback stimulatory or inhibitory sequence even before they are actually required, which is a critical piece for preventing sudden death and syncope. Moreover, the system can include vibratory stimulators within the external auditory meatus to secure their location by increasing in circumference and decreasing at specified frequencies that will provide additive stimulatory or inhibitory input to what is done electrically and with electroporation.

Alternatively or in addition, the system can use other means than electrical means, such as optogenics and small pulsed microwave, as stimulatory sequences. Such alternative means can reduce effects of headphones with transcranial magnetic stimulation on cognitive impairment and depression beyond what it will be doing on the tragus and external auditory meatus alone.

Alternatively or in addition, the system can include subcutaneous electrodes that can be placed in the region of the tragus and controlled by a watch or more distant stimulators for both stimulation and inhibition.

Referring still to FIGS. 1-4, the tragus stimulation system includes a negative effector arm for the feedback circuit. The effector arm can simultaneously or sequentially block vagal output quickly. For example, the tragus stimulation system can use pulsed DC sequences that serve to temporarily and reversibly electroporate the vagal afferents. Although the system described here is primarily described to be used for the tragus, the negative effector arm of the system can be configured to be used for other external or internal autonomic afferent sites.

The system can provide an integrated feedback loop, which can be unsupervised and/or manually set. The system uses a variety of sensory inputs, examples of which include a local electroneural and thermal conductivity as a direct and surrogate marker for autonomic tone to know when to stimulate, how much to stimulate, and when to block. In addition to this primary sensor, the system can include a clip on the tragus as part of a wearable device (e.g., an integrated headphone or an external auditory meatus plug) to measure several physiological parameters, such as heart rate variability, blood pressure, estimate cardiac output, and in real time allow the optimal amount of stimulation and uniquely blockade.

As described herein, the system is configured to use electroporation to validate autonomic neural recordings. In some implementations, a very high sensitivity is required to detect neural signals. In this situation, background noise becomes an important confounding feature. However, small phased DC fields will either ameliorate or attenuate autonomic neural signals but have no effect or accentuate background noise. This mechanism of validating signals is integral for the feedback loop to work.

As described herein, the system can provide real-time date neural network based learning of an individual's heart rate variability and other sensory parameter profile such that if there is an adverse detection of autonomic tone with implication being either susceptibility to syncope or arrhythmia, then even before the actual parameter concerned drops or changes such as the onset of an arrhythmia, algorithmic neural network based prediction will allow preemptive change in the stimulatory or inhibitory sequence.

As described herein, the wearable device of the system can have connectivity with other devices, such as watches, rings, or other sensory tools to automatically modulate the stimulatory or blocking sequence.

As described herein, the system can provide unique stimulatory algorithms that can be in phase or tailored with the auditory or musical experience the individual has from the integrated headphone.

As described herein, the system operates to filter an injection of inverted pulsed phased waveforms so as to not interfere with the auditory experience and/or not add to the background noise.

It is understood that the same or similar devices, systems, methods, and principles for the tragus stimulation described herein can be used for other parts of the body including other parts of the external ear. This includes forms that can expand while serving as an in-ear but within the external auditory meatus devices that cover the entire pinna, clips to the pinna, and combination devices. Similarly, other external sites for vagal stimulation including the hand (e.g., Xiemen point), neck, and other body structures with forms that may include collars, rings, watches, gloves, socks, etc.

It is understood that the reversible electroporation can be used not only as a validation method for signals, but also as a standalone therapy. For example, delivery of a reversible electroporation can be used to treat syncope.

Figure 5:
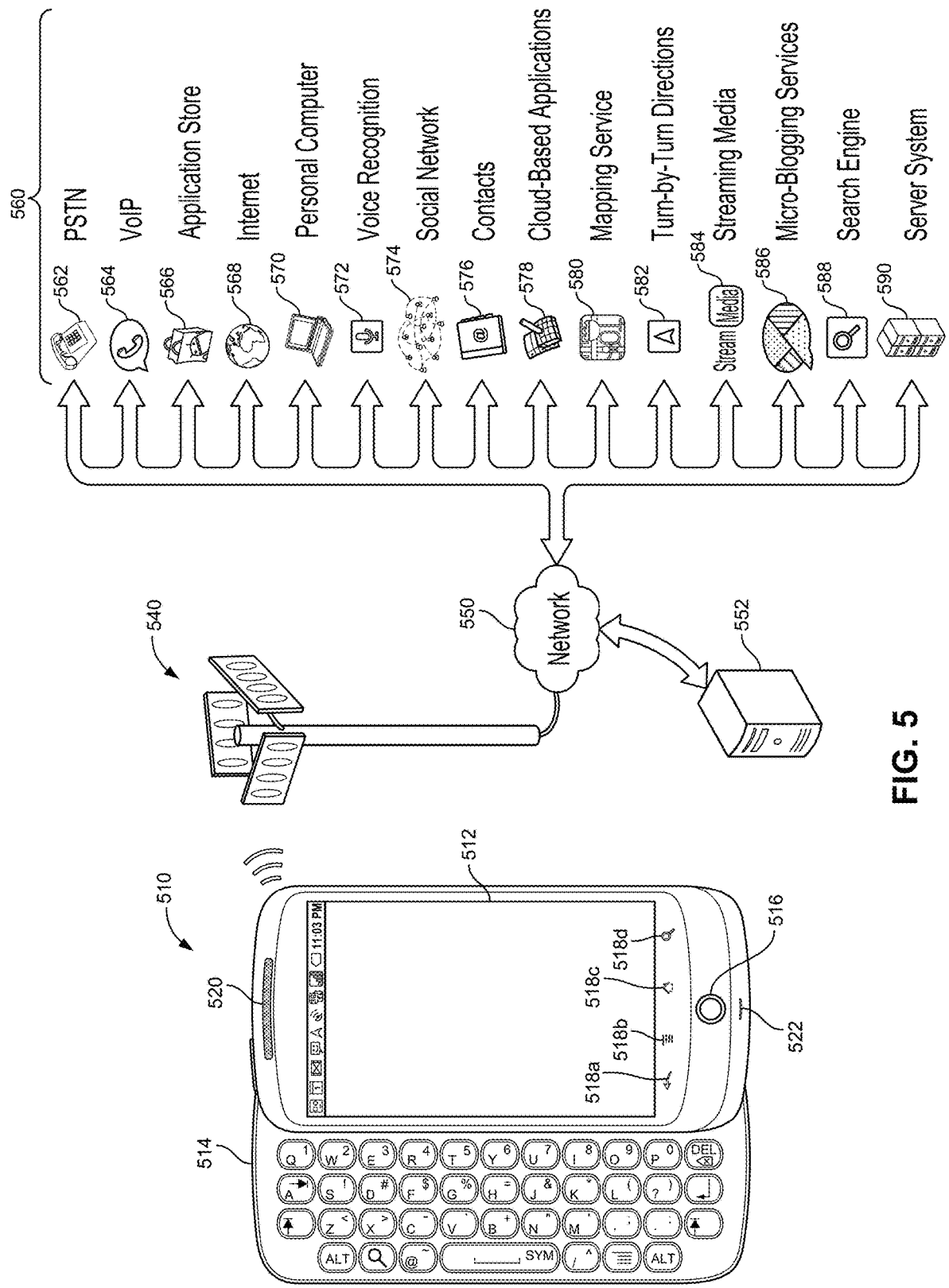
FIG. 5 is a conceptual diagram of a system that may be used to implement the systems and methods described in this document is illustrated.

Referring now to FIG. 5, a conceptual diagram of a system that may be used to implement the systems and methods described in this document is illustrated. In the system, mobile computing device 510 can wirelessly communicate with base station 540, which can provide the mobile computing device wireless access to numerous hosted services 560 through a network 550.

In this illustration, the mobile computing device 510 is depicted as a handheld mobile telephone (e.g., a smartphone, or an application telephone) that includes a touchscreen display device 512 for presenting content to a user of the mobile computing device 510 and receiving touch-based user inputs and/or presence-sensitive user input (e.g., as detected over a surface of the computing device using radar detectors mounted in the mobile computing device 510). Other visual, tactile, and auditory output components may also be provided (e.g., LED lights, a vibrating mechanism for tactile output, or a speaker for providing tonal, voice-generated, or recorded output), as may various different input components (e.g., keyboard 514, physical buttons, trackballs, accelerometers, gyroscopes, and magnetometers).

Example visual output mechanism in the form of display device 512 may take the form of a display with resistive or capacitive touch capabilities. The display device may be for displaying video, graphics, images, and text, and for coordinating user touch input locations with the location of displayed information so that the device 510 can associate user contact at a location of a displayed item with the item. The mobile computing device 510 may also take alternative forms, including as a laptop computer, a tablet or slate computer, a personal digital assistant, an embedded system (e.g., a car navigation system), a desktop personal computer, or a computerized workstation.

An example mechanism for receiving user-input includes keyboard 514, which may be a full qwerty keyboard or a traditional keypad that includes keys for the digits '0-9', '*', and '#.' The keyboard 514 receives input when a user physically contacts or depresses a keyboard key. User manipulation of a trackball 516 or interaction with a track pad enables the user to supply directional and rate of movement information to the mobile computing device 510 (e.g., to manipulate a position of a cursor on the display device 512).

The mobile computing device 510 may be able to determine a position of physical contact with the touchscreen display device 512 (e.g., a position of contact by a finger or a stylus). Using the touchscreen 512, various "virtual" input mechanisms may be produced, where a user interacts with a graphical user interface element depicted on the touchscreen 512 by contacting the graphical user interface element. An example of a "virtual" input mechanism is a "software keyboard," where a keyboard is displayed on the touchscreen and a user selects keys by pressing a region of the touchscreen 512 that corresponds to each key.

The mobile computing device 510 may include mechanical or touch sensitive buttons 518a-d. Additionally, the mobile computing device may include buttons for adjusting volume output by the one or more speakers 520, and a button for turning the mobile computing device on or off. A microphone 522 allows the mobile computing device 510 to convert audible sounds into an electrical signal that may be digitally encoded and stored in computer-readable memory, or transmitted to another computing device. The mobile computing device 510 may also include a digital compass, an accelerometer, proximity sensors, and ambient light sensors.

An operating system may provide an interface between the mobile computing device's hardware (e.g., the input/output mechanisms and a processor executing instructions retrieved from computer-readable medium) and software. Example operating systems include ANDROID, CHROME, IOS, MAC OS X, WINDOWS 7, WINDOWS PHONE 7, SYMBIAN, BLACKBERRY, WEBOS, a variety of UNIX operating systems; or a proprietary operating system for computerized devices. The operating system may provide a platform for the execution of application programs that facilitate interaction between the computing device and a user.

The mobile computing device 510 may present a graphical user interface with the touchscreen 512. A graphical user interface is a collection of one or more graphical interface elements and may be static (e.g., the display appears to remain the same over a period of time), or may be dynamic (e.g., the graphical user interface includes graphical interface elements that animate without user input).

A graphical interface element may be text, lines, shapes, images, or combinations thereof. For example, a graphical interface element may be an icon that is displayed on the desktop and the icon's associated text. In some examples, a graphical interface element is selectable with user-input. For example, a user may select a graphical interface element by pressing a region of the touchscreen that corresponds to a display of the graphical interface element. In some examples, the user may manipulate a trackball to highlight a single graphical interface element as having focus. User-selection of a graphical interface element may invoke a pre-defined action by the mobile computing device. In some examples, selectable graphical interface elements further or alternatively correspond to a button on the keyboard 504. User-selection of the button may invoke the pre-defined action.

In some examples, the operating system provides a "desktop" graphical user interface that is displayed after turning on the mobile computing device 510, after activating the mobile computing device 510 from a sleep state, after "unlocking" the mobile computing device 510, or after receiving user-selection of the "home" button 518*c*. The desktop graphical user interface may display several graphical interface elements that, when selected, invoke corresponding application programs. An invoked application program may present a graphical interface that replaces the desktop graphical user interface until the application program terminates or is hidden from view.

User-input may influence an executing sequence of mobile computing device 510 operations. For example, a single-action user input (e.g., a single tap of the touchscreen, swipe across the touchscreen, contact with a button, or combination of these occurring at a same time) may invoke an operation that changes a display of the user interface. Without the user-input, the user interface may not have changed at a particular time. For example, a multi-touch user input with the touchscreen 512 may invoke a mapping application to "zoom-in" on a location, even though the mapping application may have by default zoomed-in after several seconds.

The desktop graphical interface can also display "widgets." A widget is one or more graphical interface elements that are associated with an application program that is executing, and that display on the desktop content controlled by the executing application program. A widget's application program may launch as the mobile device turns on. Further, a widget may not take focus of the full display. Instead, a widget may only "own" a small portion of the desktop, displaying content and receiving touchscreen user-input within the portion of the desktop.

The mobile computing device 510 may include one or more location-identification mechanisms. A location-identification mechanism may include a collection of hardware and software that provides the operating system and application programs an estimate of the mobile device's geographical position. A location-identification mechanism may employ satellite-based positioning techniques, base station transmitting antenna identification, multiple base station triangulation, internet access point IP location determinations, inferential identification of a user's position based on search engine queries, and user-supplied identification of location (e.g., by receiving user a "check in" to a location).

The mobile computing device 510 may include other applications, computing sub-systems, and hardware. A call handling unit may receive an indication of an incoming telephone call and provide a user the capability to answer the incoming telephone call. A media player may allow a user to listen to music or play movies that are stored in local memory of the mobile computing device 510. The mobile device 510 may include a digital camera sensor, and corresponding image and video capture and editing software. An internet browser may enable the user to view content from a web page by typing in an addresses corresponding to the web page or selecting a link to the web page.

The mobile computing device 510 may include an antenna to wirelessly communicate information with the base station 540. The base station 540 may be one of many base stations in a collection of base stations (e.g., a mobile telephone cellular network) that enables the mobile computing device 510 to maintain communication with a network 550 as the mobile computing device is geographically moved. The computing device 510 may alternatively or additionally communicate with the network 550 through a Wi-Fi router or a wired connection (e.g., ETHERNET, USB, or FIREWIRE). The computing device 510 may also wirelessly communicate with other computing devices using BLUETOOTH protocols, or may employ an ad-hoc wireless network.

A service provider that operates the network of base stations may connect the mobile computing device 510 to the network 550 to enable communication between the mobile computing device 510 and other computing systems that provide services 560. Although the services 560 may be provided over different networks (e.g., the service provider's internal network, the Public Switched Telephone Network, and the Internet), network 550 is illustrated as a single network. The service provider may operate a server system 552 that routes information packets and voice data between the mobile computing device 510 and computing systems associated with the services 560.

The network 550 may connect the mobile computing device 510 to the Public Switched Telephone Network (PSTN) 562 in order to establish voice or fax communication between the mobile computing device 510 and another computing device. For example, the service provider server system 552 may receive an indication from the PSTN 562 of an incoming call for the mobile computing device 510. Conversely, the mobile computing device 510 may send a communication to the service provider server system 552 initiating a telephone call using a telephone number that is associated with a device accessible through the PSTN 562.

The network 550 may connect the mobile computing device 510 with a Voice over Internet Protocol (VoIP) service 564 that routes voice communications over an IP network, as opposed to the PSTN. For example, a user of the mobile computing device 510 may invoke a VoIP application and initiate a call using the program. The service provider server system 552 may forward voice data from the call to a VoIP service, which may route the call over the internet to a corresponding computing device, potentially using the PSTN for a final leg of the connection.

An application store 566 may provide a user of the mobile computing device 510 the ability to browse a list of remotely stored application programs that the user may download over the network 550 and install on the mobile computing device 510. The application store 566 may serve as a repository of applications developed by third-party application developers. An application program that is installed on the mobile computing device 510 may be able to communicate over the network 550 with server systems that are designated for the application program. For example, a VoIP application program may be downloaded from the Application Store 566, enabling the user to communicate with the VoIP service 564.

The mobile computing device 510 may access content on the internet 568 through network 550. For example, a user of the mobile computing device 510 may invoke a web browser application that requests data from remote computing devices that are accessible at designated universal resource locations. In various examples, some of the services 560 are accessible over the internet.

The mobile computing device may communicate with a personal computer 570. For example, the personal computer 570 may be the home computer for a user of the mobile computing device 510. Thus, the user may be able to stream media from his personal computer 570. The user may also view the file structure of his personal computer 570, and transmit selected documents between the computerized devices.

A voice recognition service 572 may receive voice communication data recorded with the mobile computing device's microphone 522, and translate the voice communication into corresponding textual data. In some examples, the translated text is provided to a search engine as a web query, and responsive search engine search results are transmitted to the mobile computing device 510.

The mobile computing device 510 may communicate with a social network 574. The social network may include numerous members, some of which have agreed to be related as acquaintances. Application programs on the mobile computing device 510 may access the social network 574 to retrieve information based on the acquaintances of the user of the mobile computing device. For example, an "address book" application program may retrieve telephone numbers for the user's acquaintances. In various examples, content may be delivered to the mobile computing device 510 based on social network distances from the user to other members in a social network graph of members and connecting relationships. For example, advertisement and news article content may be selected for the user based on a level of interaction with such content by members that are "close" to the user (e.g., members that are "friends" or "friends of friends").

The mobile computing device 510 may access a personal set of contacts 576 through network 550. Each contact may identify an individual and include information about that individual (e.g., a phone number, an email address, and a birthday). Because the set of contacts is hosted remotely to the mobile computing device 510, the user may access and maintain the contacts 576 across several devices as a common set of contacts.

The mobile computing device 510 may access cloud-based application programs 578. Cloud-computing provides application programs (e.g., a word processor or an email program) that are hosted remotely from the mobile computing device 510, and may be accessed by the device 510 using a web browser or a dedicated program. Example cloud-based application programs include GOOGLE DOCS word processor and spreadsheet service, GOOGLE GMAIL webmail service, and PICASA picture manager.

Mapping service 580 can provide the mobile computing device 510 with street maps, route planning information, and satellite images. An example mapping service is GOOGLE MAPS. The mapping service 580 may also receive queries and return location-specific results. For example, the mobile computing device 510 may send an estimated location of the mobile computing device and a user-entered query for "pizza places" to the mapping service 580. The mapping service 580 may return a street map with "markers" superimposed on the map that identify geographical locations of nearby "pizza places."

Turn-by-turn service 582 may provide the mobile computing device 510 with turn-by-turn directions to a user-supplied destination. For example, the turn-by-turn service 582 may stream to device 510 a street-level view of an estimated location of the device, along with data for providing audio commands and superimposing arrows that direct a user of the device 510 to the destination.

Various forms of streaming media 584 may be requested by the mobile computing device 510. For example, computing device 510 may request a stream for a pre-recorded video file, a live television program, or a live radio program. Example services that provide streaming media include YOUTUBE and PANDORA.

A micro-blogging service 586 may receive from the mobile computing device 510 a user-input post that does not identify recipients of the post. The micro-blogging service 586 may disseminate the post to other members of the micro-blogging service 586 that agreed to subscribe to the user.

A search engine 588 may receive user-entered textual or verbal queries from the mobile computing device 510, determine a set of internet-accessible documents that are responsive to the query, and provide to the device 510 information to display a list of search results for the responsive documents. In examples where a verbal query is received, the voice recognition service 572 may translate the received audio into a textual query that is sent to the search engine.

These and other services may be implemented in a server system 590. A server system may be a combination of hardware and software that provides a service or a set of services. For example, a set of physically separate and networked computerized devices may operate together as a logical server system unit to handle the operations necessary to offer a service to hundreds of computing devices. A server system is also referred to herein as a computing system.

In various implementations, operations that are performed "in response to" or "as a consequence of" another operation (e.g., a determination or an identification) are not performed if the prior operation is unsuccessful (e.g., if the determination was not performed). Operations that are performed "automatically" are operations that are performed without user intervention (e.g., intervening user input). Features in this document that are described with conditional language may describe implementations that are optional. In some examples, "transmitting" from a first device to a second device includes the first device placing data into a network for receipt by the second device, but may not include the second device receiving the data. Conversely, "receiving" from a first device may include receiving the data from a network, but may not include the first device transmitting the data.

"Determining" by a computing system can include the computing system requesting that another device perform the determination and supply the results to the computing system. Moreover, "displaying" or "presenting" by a computing system can include the computing system sending data for causing another device to display or present the referenced information.

Figure 6:
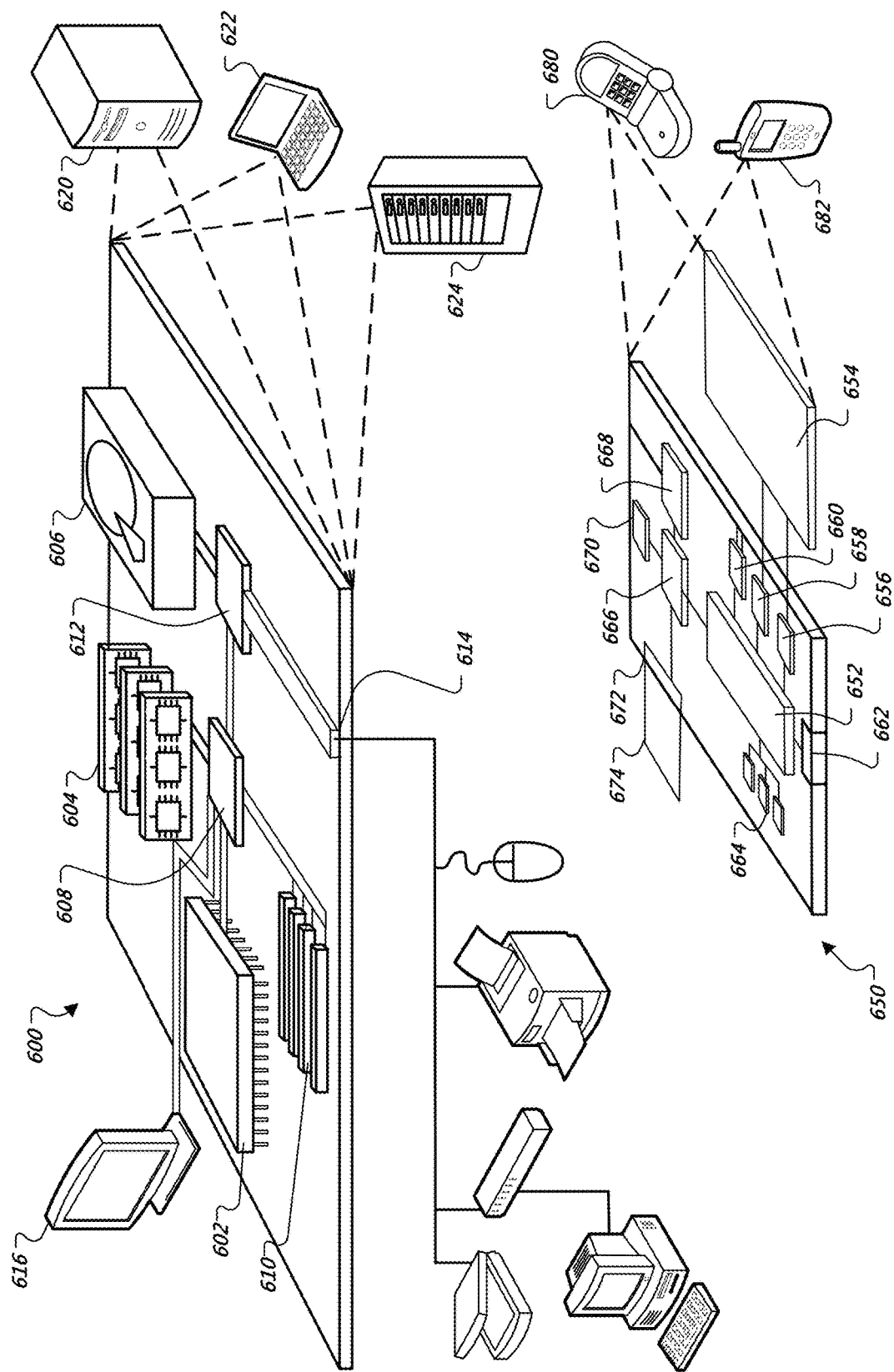
FIG. 6 is a block diagram of computing devices that may be used to implement the systems and methods described in this document.

FIG. 6 is a block diagram of computing devices 600, 650 that may be used to implement the systems and methods described in this document, as either a client or as a server or plurality of servers. Computing device 600 is intended to represent various forms of digital computers, such as laptops, desktops, workstations, personal digital assistants, servers, blade servers, mainframes, and other appropriate computers. Computing device 650 is intended to represent various forms of mobile devices, such as personal digital assistants, cellular telephones, smartphones, and other similar computing devices. The components shown here, their connections and relationships, and their functions, are meant to be examples only, and are not meant to limit implementations described and/or claimed in this document.

Computing device 600 includes a processor 602, memory 604, a storage device 606, a high-speed interface 608 connecting to memory 604 and high-speed expansion ports 610, and a low speed interface 612 connecting to low speed bus 614 and storage device 606. Each of the components 602, 604, 606, 608, 610, and 612, are interconnected using various busses, and may be mounted on a common motherboard or in other manners as appropriate. The processor 602 can process instructions for execution within the computing device 600, including instructions stored in the memory 604 or on the storage device 606 to display graphical information for a GUI on an external input/output device, such as display 616 coupled to high-speed interface 608. In other implementations, multiple processors and/or multiple buses may be used, as appropriate, along with multiple memories and types of memory. Also, multiple computing devices 600 may be connected, with each device providing portions of the necessary operations (e.g., as a server bank, a group of blade servers, or a multi-processor system).

The memory 604 stores information within the computing device 600. In one implementation, the memory 604 is a volatile memory unit or units. In another implementation, the memory 604 is a non-volatile memory unit or units. The memory 604 may also be another form of computer-readable medium, such as a magnetic or optical disk.

The storage device 606 is capable of providing mass storage for the computing device 600. In one implementation, the storage device 606 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 604, the storage device 606, or memory on processor 602.

The high-speed controller 608 manages bandwidth-intensive operations for the computing device 600, while the low speed controller 612 manages lower bandwidth-intensive operations. Such allocation of functions is an example only. In one implementation, the high-speed controller 608 is coupled to memory 604, display 616 (e.g., through a graphics processor or accelerator), and to high-speed expansion ports 610, which may accept various expansion cards (not shown). In the implementation, low-speed controller 612 is coupled to storage device 606 and low-speed expansion port 614. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 600 may be implemented in a number of different forms, as shown in the figure. For example, it may be implemented as a standard server 620, or multiple times in a group of such servers. It may also be implemented as part of a rack server system 624. In addition, it may be implemented in a personal computer such as a laptop computer 622. Alternatively, components from computing device 600 may be combined with other components in a mobile device (not shown), such as device 650. Each of such devices may contain one or more of computing device 600, 650, and an entire system may be made up of multiple computing devices 600, 650 communicating with each other.

Computing device 650 includes a processor 652, memory 664, an input/output device such as a display 654, a communication interface 666, and a transceiver 668, among other components. The device 650 may also be provided with a storage device, such as a microdrive or other device, to provide additional storage. Each of the components 650, 652, 664, 654, 666, and 668, are interconnected using various buses, and several of the components may be mounted on a common motherboard or in other manners as appropriate.

The processor 652 can execute instructions within the computing device 650, including instructions stored in the memory 664. The processor may be implemented as a chipset of chips that include separate and multiple analog and digital processors. Additionally, the processor may be implemented using any of a number of architectures. For example, the processor may be a CISC (Complex Instruction Set Computers) processor, a RISC (Reduced Instruction Set Computer) processor, or a MISC (Minimal Instruction Set Computer) processor. The processor may provide, for example, for coordination of the other components of the device 650, such as control of user interfaces, applications run by device 650, and wireless communication by device 650.

Processor 652 may communicate with a user through control interface 658 and display interface 656 coupled to a display 654. The display 654 may be, for example, a TFT (Thin-Film-Transistor Liquid Crystal Display) display or an OLED (Organic Light Emitting Diode) display, or other appropriate display technology. The display interface 656 may comprise appropriate circuitry for driving the display 654 to present graphical and other information to a user. The control interface 658 may receive commands from a user and convert them for submission to the processor 652. In addition, an external interface 662 may be provide in communication with processor 652, so as to enable near area communication of device 650 with other devices. External interface 662 may provided, for example, for wired communication in some implementations, or for wireless communication in other implementations, and multiple interfaces may also be used.

The memory 664 stores information within the computing device 650. The memory 664 can be implemented as one or more of a computer-readable medium or media, a volatile memory unit or units, or a non-volatile memory unit or units. Expansion memory 674 may also be provided and connected to device 650 through expansion interface 672, which may include, for example, a SIMM (Single In Line Memory Module) card interface. Such expansion memory 674 may provide extra storage space for device 650, or may also store applications or other information for device 650. Specifically, expansion memory 674 may include instructions to carry out or supplement the processes described above, and may include secure information also. Thus, for example, expansion memory 674 may be provide as a security module for device 650, and may be programmed with instructions that permit secure use of device 650. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 664, expansion memory 674, or memory on processor 652 that may be received, for example, over transceiver 668 or external interface 662.

Device 650 may communicate wirelessly through communication interface 666, which may include digital signal processing circuitry where necessary. Communication interface 666 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 668. In addition, short-range communication may occur, such as using a Bluetooth, WiFi, or other such transceiver (not shown). In addition, GPS (Global Positioning System) receiver module 670 may provide additional navigation- and location-related wireless data to device 650, which may be used as appropriate by applications running on device 650.

Device 650 may also communicate audibly using audio codec 660, which may receive spoken information from a user and convert it to usable digital information. Audio codec 660 may likewise generate audible sound for a user, such as through a speaker, e.g., in a handset of device 650. Such sound may include sound from voice telephone calls, may include recorded sound (e.g., voice messages, music files, etc.) and may also include sound generated by applications operating on device 650.

The computing device 650 may be implemented in a number of different forms, as shown in the figure. For example, it may be implemented as a cellular telephone 680. It may also be implemented as part of a smartphone 682, personal digital assistant, or other similar mobile device.

Additionally computing device 600 or 650 can include Universal Serial Bus (USB) flash drives. The USB flash drives may store operating systems and other applications. The USB flash drives can include input/output components, such as a wireless transmitter or USB connector that may be inserted into a USB port of another computing device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), peer-to-peer networks (having ad-hoc or static members), grid computing infrastructures, and the Internet.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A method for treating or preventing atrial fibrillation of a patient, the method comprising:
   detecting an indication of the atrial fibrillation;
   in response to the detection of the indication of the atrial fibrillation, generating, using a wearable device that is worn by the patient, a stimulatory signal, wherein the stimulatory signal is applied to a tragus area to increase vagal tone; and
   generating a reversible electroporation sequence comprising a small phased DC sequence.

2. The method of claim 1, wherein the stimulatory signal uses nanosecond pulse widths and/or relatively high amplitude.

3. The method of claim 2, wherein the stimulatory signal uses electroporation targeting sensory nerves and sensory impulses from vagus afferents.

4. The method of claim 1, wherein a frequency of the stimulatory signal is determined based on a site to which the stimulatory signal is applied.

5. The method of claim 1, further comprising:
   generating an inverse signal for the stimulatory signal; and
   creating a template for the stimulatory signal, wherein the inverse signal is generated based on the template.

6. The method of claim 1, further comprising:
   validating autonomic neural recordings based on the reversible electroporation sequence;
   generating pulsed DC sequences as a negative effector; and
   applying the pulsed DC sequences to temporarily and reversibly electroporate vagal afferents.

7. The method of claim 6, further comprising:
   detecting, using a neural network based learning algorithm, an individual's physiological parameter;
   determining that there is an adverse detection of autonomic tone; and
   enabling preemptive change in the stimulatory signal and/or the inhibitory signal.

8. The method of claim 7, further comprising detecting, using a sensor, a predetermined parameter representative of autonomic tone.

9. The method of claim 8, further comprising determining when to simulate, how much to stimulate, and when to block based on the predetermined parameter.

10. The method of claim 9, wherein the predetermined parameter includes a local electroneural and thermal conductivity, and wherein the physiological parameter includes a heart rate variability.

11. The method of claim 1, wherein the wearable device comprises:
    a housing configured to be removably worn adjacent to the tragus area;
    one or more sensors configured to detect physiological or neurological parameters; and
    one or more electrodes configured to deliver the stimulatory signal.

12. The method of claim 1, wherein the wearable device further comprises:
    a processing device; and
    a memory device storing instructions that when executed by the processing device cause the wearable device to perform the operations of claim 1.

13. The wearable device of claim 1, wherein the stimulatory signal is DC signal.

* * * * *